(12) United States Patent
Tranchina

(10) Patent No.: US 8,601,672 B2
(45) Date of Patent: Dec. 10, 2013

(54) METHOD FOR FABRICATING A STIMULATION LEAD TO REDUCE MRI HEATING

(75) Inventor: Benjamin A Tranchina, Allen, TX (US)

(73) Assignee: Advanced Neuromodulation Systems, Inc., Plano, TX (US)

(*) Notice: Subject to any disclaimer, the term of this patent is extended or adjusted under 35 U.S.C. 154(b) by 549 days.

(21) Appl. No.: 12/847,838

(22) Filed: Jul. 30, 2010

(65) Prior Publication Data

US 2011/0029054 A1   Feb. 3, 2011

Related U.S. Application Data

(60) Provisional application No. 61/230,371, filed on Jul. 31, 2009.

(51) Int. Cl.
*H01F 7/06* (2006.01)

(52) U.S. Cl.
USPC ............. 29/605; 29/602.1; 29/606; 29/755; 29/868; 264/250; 264/272.19; 336/83; 336/175; 336/192; 336/212; 336/233

(58) Field of Classification Search
USPC ......... 29/602.1, 605, 606, 755, 868; 264/250, 264/272.19; 336/83, 175, 192, 200, 212, 336/233; 57/6, 10, 13, 17, 18
See application file for complete search history.

(56) References Cited

U.S. PATENT DOCUMENTS

| | | | |
|---|---|---|---|
| 5,217,010 A | 6/1993 | Tsitlik et al. | |
| 6,985,775 B2 | 1/2006 | Reinke et al. | |
| 7,174,219 B2 | 2/2007 | Wahlstrand et al. | |
| 7,287,366 B2 * | 10/2007 | Dye et al. | 57/6 |
| 7,363,090 B2 | 4/2008 | Halperin et al. | |
| 7,388,378 B2 * | 6/2008 | Gray et al. | 324/318 |
| 7,839,146 B2 * | 11/2010 | Gray | 324/318 |
| 7,934,366 B2 * | 5/2011 | Dye et al. | 57/6 |
| 2003/0083726 A1 | 5/2003 | Zeijlemaker et al. | |
| 2003/0144716 A1 | 7/2003 | Reinke et al. | |
| 2003/0144720 A1 | 7/2003 | Villaseca et al. | |
| 2005/0027340 A1 | 2/2005 | Schrom et al. | |
| 2005/0222656 A1 | 10/2005 | Wahlstrand et al. | |
| 2005/0222657 A1 | 10/2005 | Wahlstrand et al. | |

(Continued)

OTHER PUBLICATIONS

Buchli R., et al., "Heating Effects of Metallic Implants by MRI Examinations," Magnetic Resonance in Medicine, 7, 255-261 (1988).

(Continued)

*Primary Examiner* — Paul D Kim

(57) ABSTRACT

In one embodiment, a stimulation lead comprises: a lead body of insulative material surrounding a plurality of conductors; a plurality of electrodes; and a plurality of terminals, the plurality of terminals electrically coupled to the plurality of electrodes through the plurality of conductors; wherein each conductor of the plurality of conductors is helically wound about an axis within the lead body in at least an outer portion and an inner portion relative to the axis, the outer portion comprises a first winding pitch and the inner portion comprises a second winding pitch, the second winding pitch is less than the first winding pitch, the inner portion of each respective conductor being disposed interior to the outer portions of other conductors of the plurality of conductors; wherein an impedance of each conductor of the plurality of conductors substantially reduces MRI-induced current when the stimulation lead is present in an MRI system.

12 Claims, 7 Drawing Sheets

(56) References Cited

U.S. PATENT DOCUMENTS

| | | |
|---|---|---|
| 2005/0222658 A1 | 10/2005 | Hoegh et al. |
| 2005/0222659 A1 | 10/2005 | Olsen et al. |
| 2006/0229693 A1 | 10/2006 | Bauer et al. |
| 2006/0247747 A1 | 11/2006 | Olsen et al. |
| 2006/0247748 A1 | 11/2006 | Wahlstrand et al. |
| 2007/0088416 A1 | 4/2007 | Atalar et al. |
| 2007/0112398 A1 | 5/2007 | Stevenson et al. |
| 2007/0185556 A1 | 8/2007 | Williams et al. |
| 2007/0208383 A1 | 9/2007 | Williams |
| 2007/0299490 A1 | 12/2007 | Yang et al. |
| 2008/0009905 A1 | 1/2008 | Zeijlemaker |
| 2008/0033497 A1 | 2/2008 | Bulkes et al. |
| 2008/0116997 A1 | 5/2008 | Dabney et al. |
| 2008/0119919 A1 | 5/2008 | Atalar et al. |
| 2008/0243218 A1 | 10/2008 | Bottomley et al. |
| 2008/0262584 A1 | 10/2008 | Bottomley et al. |
| 2009/0171421 A1 | 7/2009 | Atalar et al. |

OTHER PUBLICATIONS

Bhachu, Dewinder S., et al., "Implantable Pulse Generators (Pacemakers) and Electrodes: Safety in the Magnetic Resonance Imaging Scanner Environment," Journal of Magnetic Resonance Imaging, 12:201-204 (2000).

Finelli, Daniel, et al., "MR Imaging-Related Heating of Deep Brain Stimulation Electrodes: In Vitro Study," Am. J. Neuroradiol, 23:1795-1802, Nov./Dec. 2002.

Ho, Henry S., "Safety of Metallic Implants in Magnetic Resonance Imaging," Journal of Magnetic Resonance Imaging, 14: 472-477 (2001).

\* cited by examiner

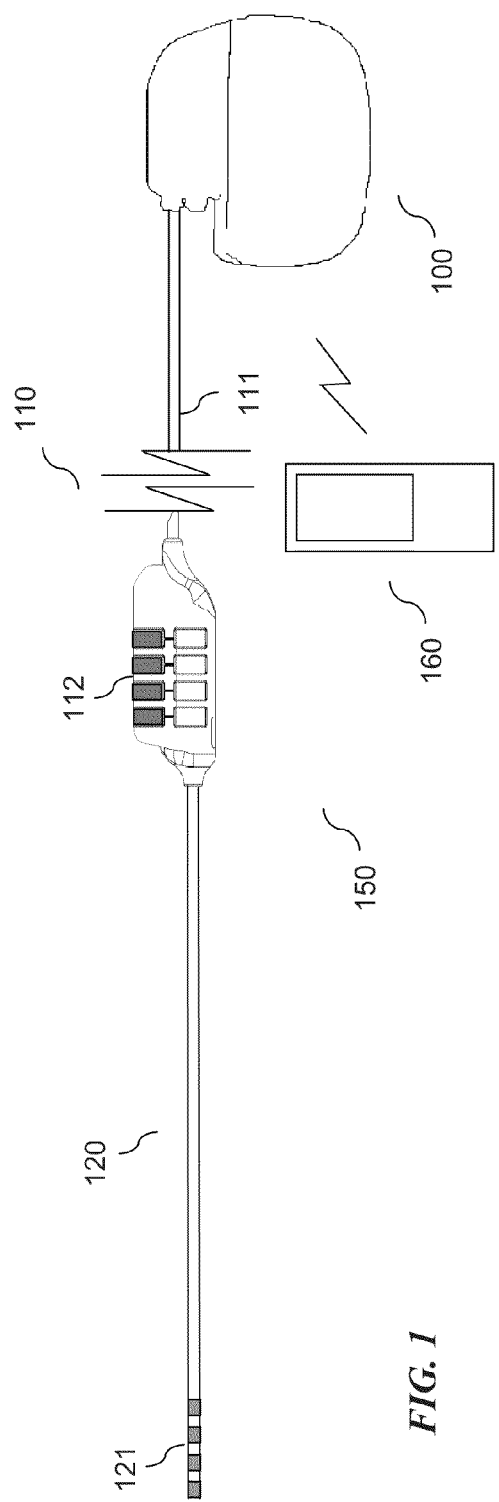
FIG. 1
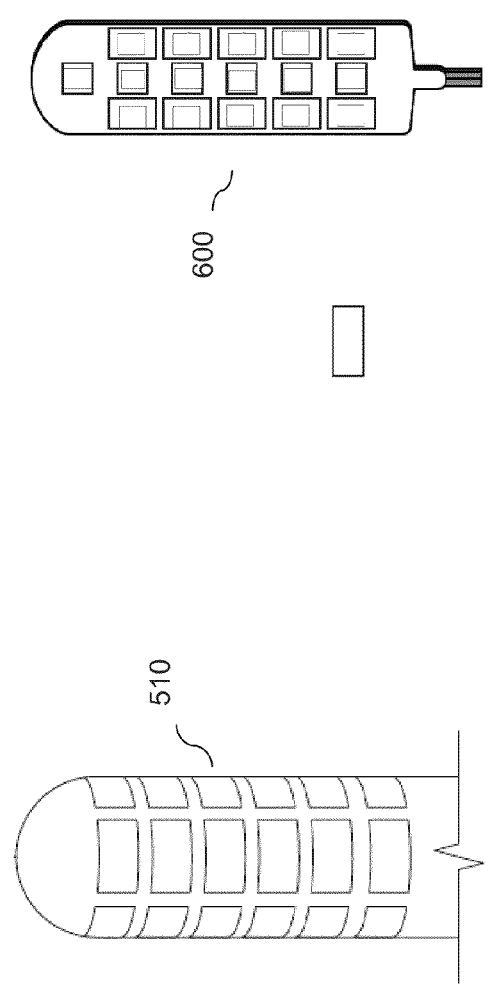
FIG. 5
FIG. 6

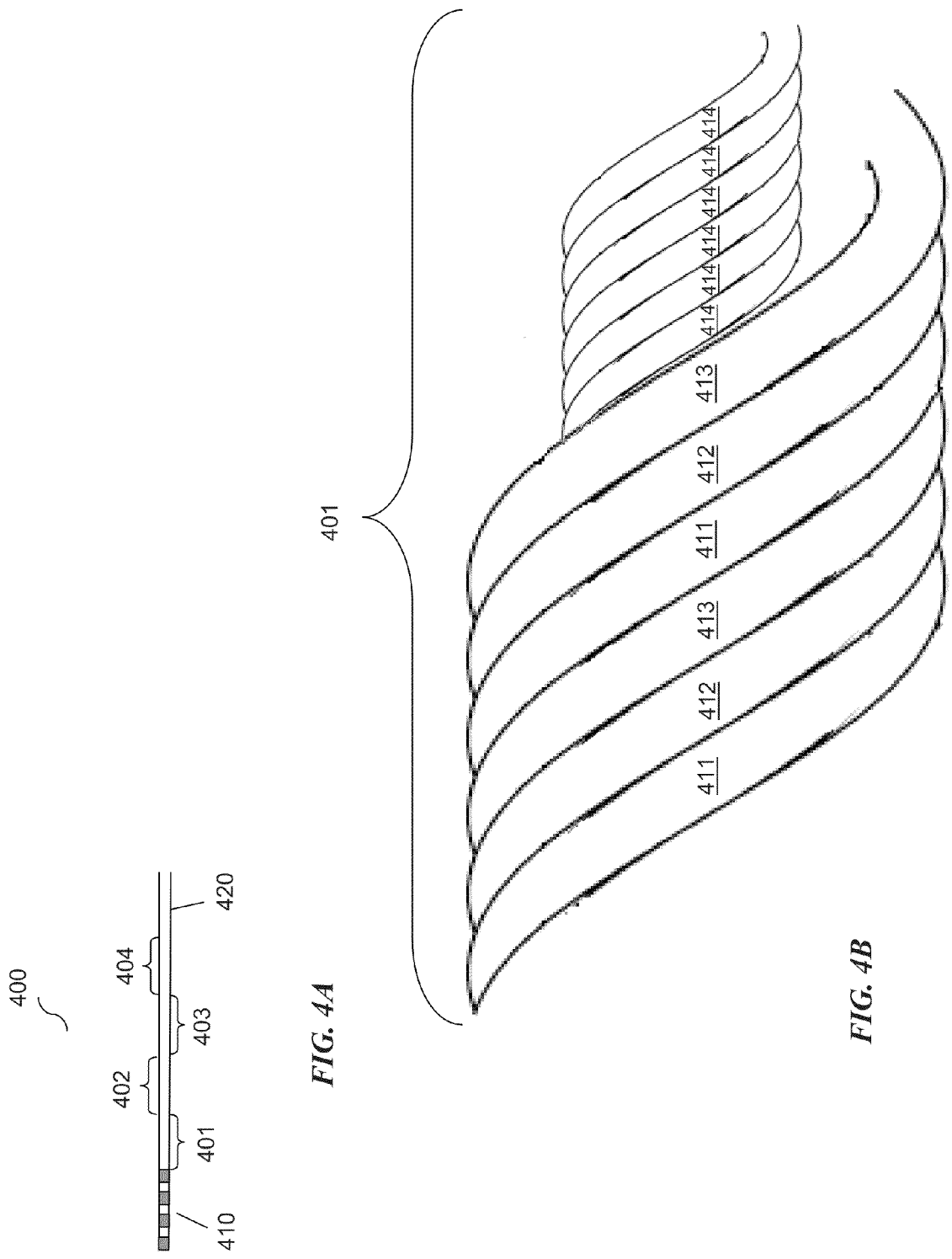

METHOD FOR FABRICATING A STIMULATION LEAD TO REDUCE MRI HEATING

CROSS-REFERENCE TO RELATED APPLICATIONS

This application claims the benefit of U.S. Provisional Application No. 61/230,371, filed Jul. 31, 2009, which is incorporated herein by reference.

TECHNICAL FIELD

The present application is generally related to limiting MRI induced current in an electrical stimulation system for patient therapy such as a neurostimulation system.

BACKGROUND

Deep brain stimulation (DBS) refers to the delivery of electrical pulses into one or several specific sites within the brain of a patient to treat various neurological disorders. For example, deep brain stimulation has been proposed as a clinical technique for treatment of chronic pain, essential tremor, Parkinson's disease (PD), dystonia, epilepsy, depression, obsessive-compulsive disorder, and other disorders.

A deep brain stimulation procedure typically involves first obtaining preoperative images of the patient's brain (e.g., using computer tomography (CT) or magnetic resonance imaging (MRI)). Using the preoperative images, the neurosurgeon can select a target region within the brain, an entry point on the patient's skull, and a desired trajectory between the entry point and the target region. In the operating room, the patient is immobilized and the patient's actual physical position is registered with a computer-controlled navigation system. The physician marks the entry point on the patient's skull and drills a burr hole at that location. Stereotactic instrumentation and trajectory guide devices are employed to control the trajectory and positioning of a stimulation lead during the surgical procedure in coordination with the navigation system.

The proximal end of the stimulation lead is tunneled underneath the skin of the patient. Often, the terminals of the stimulation lead are coupled to an "extension" lead. The extension lead is also tunneled for connection to an implantable pulse generator (IPG). The IPG is usually implanted within a subcutaneous pocket created under the skin by a physician. The IPG generates the electrical pulses for the patient therapy. The electrical pulses generated by the IPG are provided through the feedthroughs and header electrical connectors of the IPG through the extension lead to the terminals of the stimulation lead, through the wire conductors, and eventually to patient tissue through the electrodes.

There are concerns related to the compatibility of deep brain stimulation systems and other stimulation systems with magnetic resonance imaging (MRI). MRI generates cross-sectional images of the human body by using nuclear magnetic resonance (NMR). The MRI process begins with positioning the patient in a strong, uniform magnetic field. The uniform magnetic field polarizes the nuclear magnetic moments of atomic nuclei by forcing their spins into one of two possible orientations. Then an appropriately polarized pulsed RF field, applied at a resonant frequency (about 64 and 128 MHz for 1.5 T and 3.0 T MRI systems, respectively), forces spin transitions between the two orientations. Energy is imparted into the nuclei during the spin transitions. The imparted energy is radiated from the nuclei as the nuclei "relax" to their previous magnetic state. The radiated energy is received by a receiving coil and processed to determine the characteristics of the tissue from which the radiated energy originated to generate the intra-body images.

Currently, deep brain stimulation systems are designated as being contraindicated for MRI, because the time-varying magnetic RF field causes the induction of current which, in turn, can cause significant heating of patient tissue due to the presence of metal in various system components. The heating of patient tissue can cause cell necrosis. Depending upon the implant location of the electrodes of the stimulation lead, heating of the brain tissue can result in significant neurological impairment and even patient death.

The current induced by an MRI system through a stimulation lead can be "eddy current" and/or current caused by the "antenna effect." As used herein, the phrase "MRI-induced current" refers to eddy current, current caused by the antenna effect, and/or any other current generated by the time-varying fields of an MRI-system.

"Eddy current" refers to current caused by the change in magnetic flux due to the time-varying RF magnetic field across an area bounding conductive material (i.e., patient tissue). The time-varying magnetic RF field induces current within the tissue of a patient that flows in closed-paths. When a conventional pulse generator and a conventional implantable lead are placed within tissue in which eddy currents are present, the implantable lead and the pulse generator provide a low impedance path for the flow of current. Electrodes of the lead provide conductive surfaces that are adjacent to current paths within the tissue of the patient. The electrodes are coupled to the pulse generator through a wire conductor within the implantable lead. The metallic housing (the "can") of the pulse generator provides a conductive surface in the tissue in which eddy currents are present. Thus, current can flow from the tissue through the electrodes and out the metallic housing of the pulse generator. Because of the low impedance path and the relatively small surface area of each electrode, the current density in the patient tissue adjacent to the electrodes can be relatively high. Accordingly, resistive heating of the tissue adjacent to the electrodes can be high and can cause significant, irreversible tissue damage.

Also, the "antenna effect" can cause current to be induced which can result in undesired heating of tissue. Specifically, depending upon the length of the stimulation lead and its orientation relative to the time-varying magnetic RF field, the wire conductors of the stimulation lead can each function as an antenna and a resonant standing wave can be developed in each wire. A relatively large potential difference can result from the standing wave thereby causing relatively high current density and, hence, heating of tissue adjacent to the electrodes of the stimulation lead.

SUMMARY

In one embodiment, a stimulation lead comprises: a lead body of insulative material surrounding a plurality of conductors; a plurality of electrodes disposed at a distal end of the stimulation lead; and a plurality of terminals disposed at a proximal end of the stimulation lead, the plurality of terminals electrically coupled to the plurality of electrodes through the plurality of conductors; wherein each conductor of the plurality of conductors is helically wound about an axis within the lead body in at least an outer portion and an inner portion relative to the axis, the outer portion comprises a first winding pitch and the inner portion comprises a second winding pitch, the second winding pitch is less than the first winding pitch, the inner portion of each respective conductor being disposed interior to the outer portions of other conductors of the plurality of conductors; wherein an impedance of each conductor of the plurality of conductors substantially reduces MRI-induced current when the stimulation lead is present in an MRI system.

The foregoing has outlined rather broadly certain features and/or technical advantages in order that the detailed description that follows may be better understood. Additional features and/or advantages will be described hereinafter which form the subject of the claims. It should be appreciated by those skilled in the art that the conception and specific embodiment disclosed may be readily utilized as a basis for modifying or designing other structures for carrying out the same purposes. It should also be realized by those skilled in the art that such equivalent constructions do not depart from the spirit and scope of the appended claims. The novel features, both as to organization and method of operation, together with further objects and advantages will be better understood from the following description when considered in connection with the accompanying figures. It is to be expressly understood, however, that each of the figures is provided for the purpose of illustration and description only and is not intended as a definition of the limits of the appended claims.

BRIEF DESCRIPTION OF THE DRAWINGS

FIG. 1 depicts a stimulation system according to one representative embodiment.

FIGS. 4A and 4B depict a distal end of a stimulation lead according to one representative embodiment.

FIG. 5 depicts a distal end of a stimulation lead that may be employed with some representative embodiments.

FIG. 6 depicts a paddle structure that may be employed with some representative embodiments.

DETAILED DESCRIPTION

Figure 2:
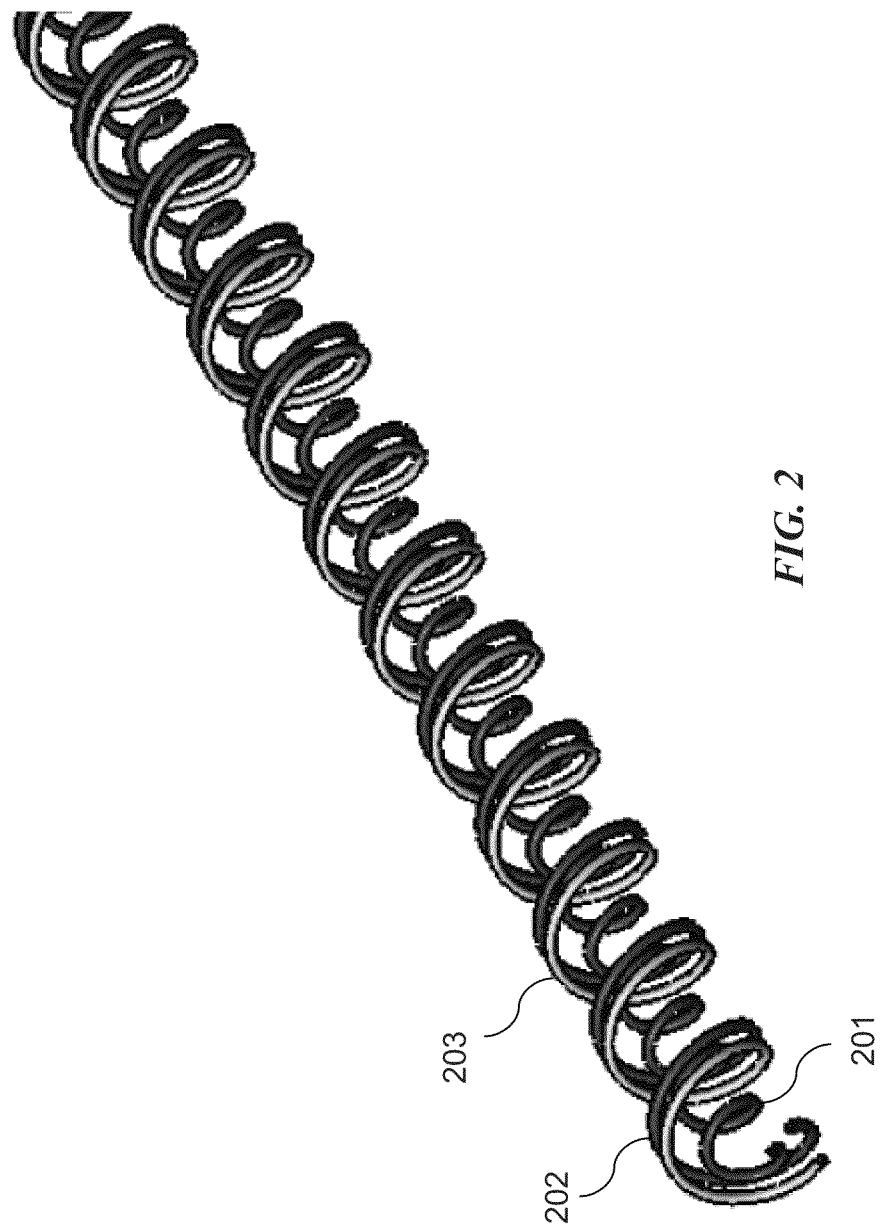
FIG. 2 depicts a portion windings of conductors for inclusion within a stimulation lead according to one representative embodiment.

FIG. 1 depicts stimulation system 150 that generates electrical pulses for application to tissue of a patient according to one representative embodiment. According to one preferred embodiment, system 150 is a deep brain stimulation system. In other embodiments, system 150 may stimulate any other tissue in a patient such as cortical brain tissue, spinal cord tissue, peripheral nerve tissue, cardiac tissue, etc.

System 150 includes implantable pulse generator 100 that is adapted to generate electrical pulses for application to tissue of a patient. Implantable pulse generator 100 typically comprises a metallic housing that encloses pulse generating circuitry, control circuitry, communication circuitry, battery, charging circuitry, etc. of the device. The control circuitry typically includes a microcontroller or other suitable processor for controlling the various other components of the device. An example of pulse generating circuitry is described in U.S. Patent Publication No. 20060170486 entitled "PULSE GENERATOR HAVING AN EFFICIENT FRACTIONAL VOLTAGE CONVERTER AND METHOD OF USE," which is incorporated herein by reference. A processor and associated charge control circuitry for an implantable pulse generator is described in U.S. Patent Publication No. 20060259098, entitled "SYSTEMS AND METHODS FOR USE IN PULSE GENERATION," which is incorporated herein by reference. Circuitry for recharging a rechargeable battery of an implantable pulse generator using inductive coupling and external charging circuits are described in U.S. patent Ser. No. 11/109,114, entitled "IMPLANTABLE DEVICE AND SYSTEM FOR WIRELESS COMMUNICATION," which is incorporated herein by reference. An example of a DBS implantable pulse generator is the LIBRA® pulse generator available from St. Jude Medical Neuromodulation Division (Plano, Tex.). Examples of commercially available implantable pulse generators for spinal cord stimulation are the EON® and EON® MINI pulse generators available from St. Jude Medical Neuromodulation Division.

Stimulation system 150 further comprises stimulation lead 120. Stimulation lead 120 comprises a lead body of insulative material about a plurality of conductors that extend from a proximal end of lead 120 to its distal end. Any suitable wire for biomedical applications may be employed. For example, wires formed of multi-strands of drawn-filled tubes (DFT) with a thin coating of a higher durometer insulator (e.g., perfluoroalkoxyethylene (PFA)) may be employed. The conductors electrically couple a plurality of electrodes 121 to a plurality of terminals (not shown) of lead 120. The terminals are adapted to receive electrical pulses and the electrodes 121 are adapted to apply stimulation pulses to tissue of the patient. Also, sensing of physiological electrical activity may occur through electrodes 121, the conductors, and the terminals. Additionally or alternatively, various sensors (not shown) may be located near the distal end of stimulation lead 120 to detect other signals and/or chemicals or substances. The sensors may be electrically coupled to terminals through conductors within the lead body 111. Examples of lead body fabrication, electrode fabrication, and terminal fabrication are discussed in U.S. Pat. No. 6,216,045 and U.S. Patent Publication Nos. 20050027339 which are incorporated herein by reference.

Stimulation system 150 may optionally comprise extension lead 110 as shown in FIG. 1. Extension lead 110 is adapted to connect between pulse generator 100 and stimulation lead 120. That is, electrical pulses are generated by pulse generator 100 and provided to extension lead 110 via a plurality of terminals (not shown) on the proximal end of extension lead 110. The electrical pulses are conducted through conductors within lead body 111 to housing 112. Housing 112 includes a plurality of electrical connectors (e.g., "Bal-Seal" connectors) that are adapted to connect to the terminals of lead 120. Thereby, the pulses originating from pulse generator 100 and conducted through the conductors of lead body 111 are provided to stimulation lead 120. The pulses are then conducted through the conductors of lead 120 and applied to tissue of a patient via electrodes 121.

In practice, stimulation lead 120 is implanted within a suitable location within a patient adjacent to tissue of a patient to treat the patient's particular disorder(s). For example, in deep brain stimulation for Parkinson's disease, electrodes 121 may be implanted within or immediately adjacent to the subthalamic nucleus. The proximal portion of the lead body extends away from the implant site and is, eventually, tunneled underneath the skin to a secondary location. Housing 112 of extension lead 110 is coupled to the terminals of lead 120 at the secondary location and is implanted at that secondary location. Lead body 111 of extension lead 110 is tunneled to a third location for connection with pulse generator 100 (which is implanted at the third location).

Controller 160 is a device that permits the operations of pulse generator 100 to be controlled by a clinician or a patient after pulse generator 100 is implanted within a patient. Controller 160 can be implemented by utilizing a suitable handheld processor-based system that possesses wireless communication capabilities. The wireless communication functionality can be integrated within the handheld device package or provided as a separate attachable device. The interface functionality of controller 160 is implemented using suitable software code for interacting with the clinician and using the wireless communication capabilities to conduct communications with pulse generator 100.

Controller 160 preferably provides one or more user interfaces that are adapted to allow a clinician to efficiently define one or more stimulation programs to treat the patient's disorder(s). Each stimulation program may include one or more sets of stimulation parameters including pulse amplitude, pulse width, pulse frequency, etc. Pulse generator 100 modifies its internal parameters in response to the control signals from controller 160 to vary the stimulation characteristics of stimulation pulses transmitted through stimulation lead 120 to the tissue of the patient.

System 150 differs from conventional neurostimulation systems in that system 150 mitigates or eliminates heating that would otherwise occur within the time-varying fields of an MRI system such as maintaining the temperature rise in adjacent tissue under 5° C. In one embodiment, system 150 is adapted to maintain the temperature rise of tissue adjacent to electrodes in a 1.5 T or 3 T MRI system between 1° C. to 2° C. In another embodiment, the temperature rise of such tissue is maintained below 1° C. In yet another embodiment, the temperature rise of such tissue is maintained below 0.5° C. To reduce the temperature rise of such tissue, a portion of each conductors within the lead body of stimulation 120 is wound within the lead body to form an inductor that provides a relatively high impedance at MRI frequencies (e.g., approximately 2500 Ohms or more at 64 MHz) and provides a relatively low impedance for stimulation frequencies. In an alternative embodiment, a portion of each conductor within lead body 111 of extension lead 110 are wound within lead body 111 in the same manner. The inductance of a tightly coiled portion of a coiled inductor and, hence, its impedance at a given MRI frequency can be implemented by appropriately selecting the number of coils of the coiled portion, the cross-sectional area of the coils, and the length of the coiled portion as is well known. Also, coiled wires may exhibit parasitic capacitance and quasi self-resonance which may be taken into account when adapting the coil portion to obtain a desired amount of impedance at MRI frequencies.

FIG. 2 depicts a plurality of conductors 201, 202, and 203 wound according to one representative embodiment. FIG. 2 is intended to only depict a limited segment of the winding of conductors for inclusion within a lead body. Further segments of windings may be located proximal and/or distal to the shown segment as will be discussed below. Also, for the sake of clarity in FIG. 2, only a limited number of conductors are shown. Stimulation leads may be fabricated in a similar manner to include any suitable number of conductors. Further, FIG. 2 depicts conductors 201, 202, and 203 wound in an expanded configuration for the sake of clarity. It is contemplated that fabrication of a lead according to some embodiments would involve helically winding the conductors in a more compact manner than shown in FIG. 2.

As shown in FIG. 2, conductor 201 is helically wound about a central axis at a first radial distance. Also, conductors 202 and 203 are helically wound about the central axis at a second radial distance. The second radial distance is greater than the first radial distance and conductor 201 is therefore helically wound within conductors 201 and 202.

In preferred embodiments, conductor 201 is wound more tightly than conductors 202 and 203. Specifically, the pitch between successive turns of conductor 201 is relatively small as compared to successive turns of conductors 202 and 203. In some embodiments, adjacent turns of conductor 201 may be in contact with each other. By tightly winding a segment of conductor 201, the impedance of the tightly wound segment of conductor 201 may be increased. Preferably, the tightly wound segment of conductor 201 provides sufficient impedance at MRI frequencies to significantly reduce MRI-induced current flow through conductor 201.

Figure 3:
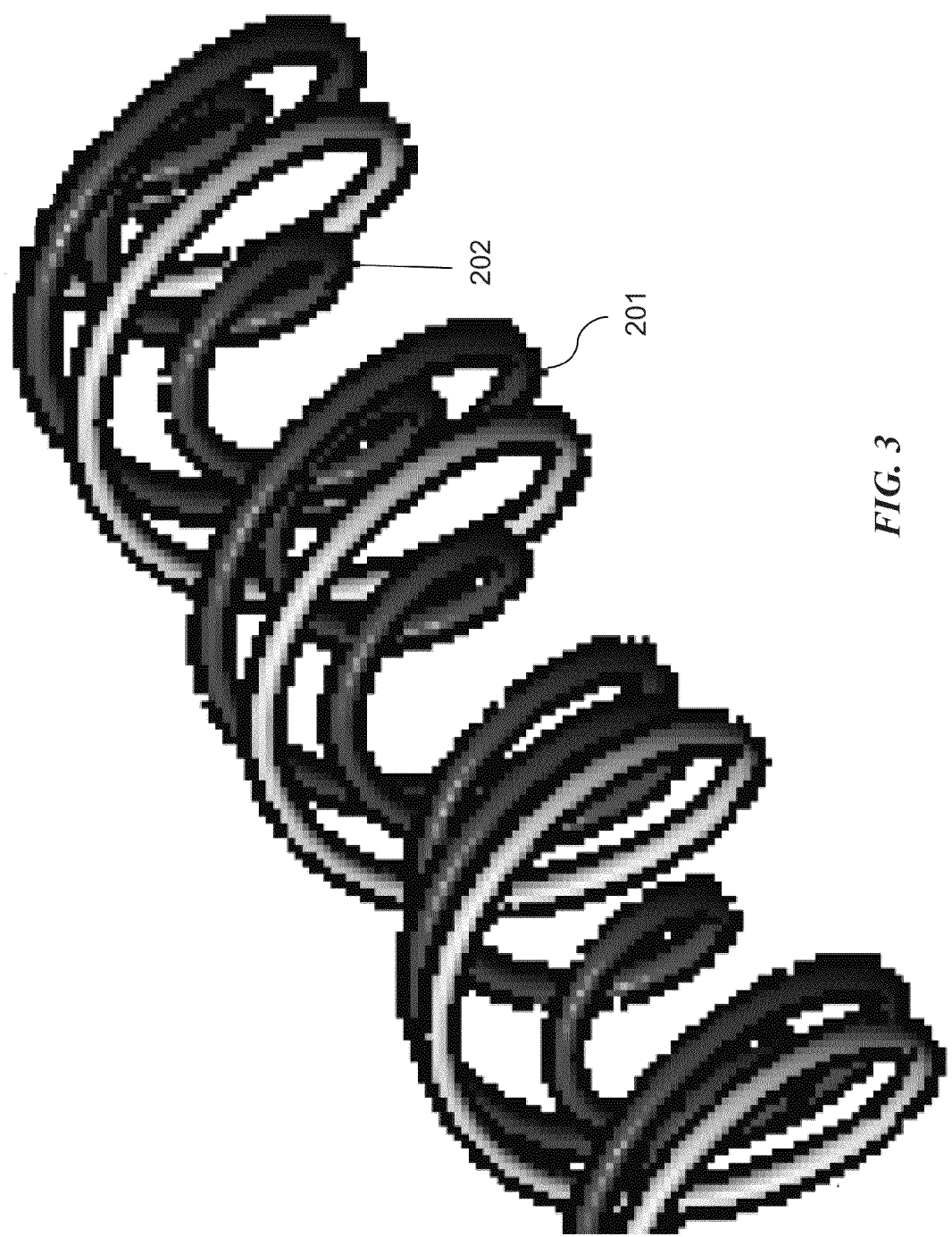
FIG. 3 depicts another portion windings of conductors for inclusion within a stimulation lead according to one representative embodiment.

Preferably, each conductor of a stimulation lead is provided with a segment where the respective conductor is brought into the interior of the windings of the other conductors and is more tightly helically wound to provide the higher impedance. FIG. 3 depicts a transition area where conductor 201 exits the inner winding portion and returns to the outer winding portion and conductor 202 enters the inner winding portion from the outer winding portion. When conductor 202 enters the inner winding portion, the pitch of the winding of conductor 202 is preferably decreased in order to increase the impedance provided by the inner winding segment of conductor 202.

FIG. 4A depicts distal portion 400 of a stimulation lead according to one representative embodiment. As shown in FIG. 4A, four electrodes 410 are provided at the distal portion of the stimulation lead. A conductor (see conductors 411, 412, 413, and 414 in FIG. 4B) is preferably provided within lead body 420 for each electrode 410. An inductor is preferably formed in each conductor by tightly winding the respective conductor within the other conductors within a respective segment of lead body 420. For example, the conductor electrically coupled to the first electrode may be tightly wound within the other three conductors within segment 401 of lead body 420. Likewise, the other three conductors may be wound in a similar manner within segments 402, 403, and 404, respectively.

FIG. 4B depicts a "cut-away" view of a portion of segment 401 according to one representative embodiment. As shown in FIG. 4B, conductors 411, 412, and 413 are helically wound in a repeating pattern at a first radial distance from the central axis of the lead. For example, each consecutive turn of conductor 411 is separated by some distance and turns of conductors 412 and 413 are interposed between consecutive turns of conductor 411. Although conductors 411, 412, and 413 are shown to be in contact with each other, conductors 411, 412, and 413 could be spaced apart. Also, spacing may be provided between groups of windings of conductors 411, 412, and 413. In the cut-away view, conductor 414 is shown more tightly wound than conductors 411, 412, and 413 and is disposed at a second, smaller radial distance from the central axis within the windings of conductors 411, 412, and 413. As shown in this embodiment, adjacent turns of conductor 414 contact each other, although some small amount of spacing could be utilized according to other embodiments. Although in some embodiments, a greater amount of impedance is provided for a given wire when a portion of the wire is wound within the other wire conductors, other embodiments may wind the conductors in other configurations. For example, a portion of a single wire may be tightly wound at a greater outside diameter in a tightly wound manner to provide greater inductance where that portion of the single wire is disposed at a greater radial distance from a central axis than the other wires at that lead segment. In such an embodiment, each conductor wire would possess a tightly wound portion at the outside radial distance to provide the appropriate impedance. Other portions of the lead would be similar to the other embodiments discussed herein.

Although only four electrodes and four conductors are shown in FIGS. 4A and 4B, any suitable number of electrodes and conductors may be provided with each corresponding conductor wound within the lead body to form an inductor to minimize or reduce MRI-induced current. Although the winding segments of the conductors are shown in FIG. 4A as being implemented at the distal end of the stimulation lead, the inductor portions may be formed at any suitable locations within the lead body according to other embodiments. Also, although only one winding segment has been discussed per conductor, multiple inductor segments may be formed for each conductor along the length of the lead body according to other embodiments. For example, a repeating pattern of inductors could be formed. Also, the multiple inductors for a given conductor may be spaced at distances possessing advantageous filtering characteristics (e.g., at about ¼ distance of the MRI wavelength).

The electrodes of a stimulation lead according to some embodiments may be ring electrodes that fully circumscribe the lead body. Electrodes of a stimulation lead according to other embodiments may be segmented electrodes (such as electrodes 510 shown in FIG. 5) that only span a limited angular range of the lead body. For example, at a given position longitudinally along the lead body, three electrodes can be provided with each electrode covering respective segments of less than 120° about the outer diameter of the lead body. By selecting between such electrodes, the electrical field generated by stimulation pulses can be more precisely controlled and, hence, stimulation of undesired tissue can be more easily avoided. Segmented electrodes may be useful for a number of therapies. For example, in deep brain stimulation, segmented electrodes permit more precise targeting of the neural tissue associated with a patient's disorder. In other embodiments, the electrodes may be disposed on a paddle structure (such paddle 600 shown in FIG. 6) provided at the distal end of the stimulation lead.

Stimulation leads may be fabricated according to some representative embodiments utilizing any suitable winding mechanisms now known or later developed. Stimulation leads may be even be fabricated by manually winding conductors of the stimulation lead about a mandrel or small diameter medical tubing with inner and outer winding portions. The manual winding may be assisted using suitably adapted fixtures to hold the various conductors whereby certain conductors may be held in an outer configuration while one or more conductors may be disposed in an inner configuration on the fixture(s) to permit the inner winding inductive segments to be formed.

Figure 7:
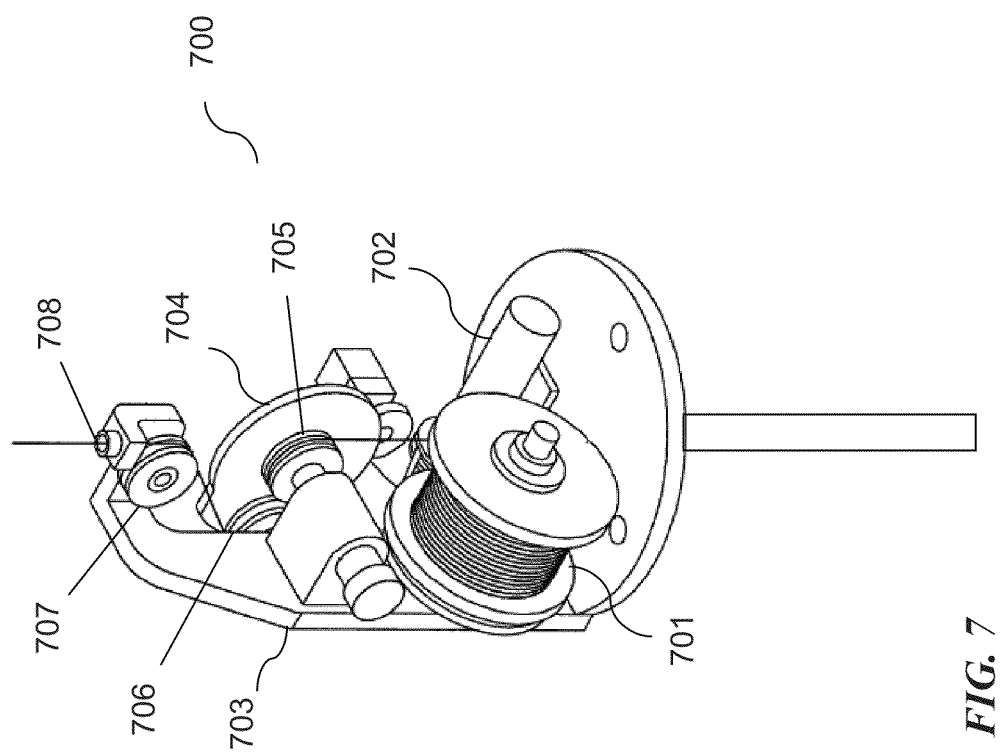
FIG. 7 depicts a wire release subassembly for use in an automated winding system according to some representative embodiments.

In other embodiments, an automated winding systems may be employed to wind conductors for lead fabrication. FIG. 7 depicts wire release subassembly 700 for controllably releasing wire in an automated wire winding system. Subassembly 700 is also shown and described in U.S. Pat. No. 7,287,366 which is incorporated herein by reference. As shown in FIG. 7, wire release subassembly 700 comprises spool 701 for maintaining a substantial length of conductor wire to be released. The wires preferably comprise an insulative coating such as PFA. Other additional coatings of insulative material may be provided such as CARBOSIL®. Such other coatings may form part of the lead body during subsequent thermal processing to fuse the coatings with other insulative material as known in the art. Electrical motor 702 drives spool 701 to release (or take up) the wire in a controller manner. That is, the current or voltage provided to electrical motor 702 controls the speed of the motor and, hence, the release rate of subassembly 700. The conductor wire follows a path defined by dancer arm 704 which is rotatably mounted to frame 703. Dancer arm 704 includes guide wheels 705 and 706 about which the conductor wire travels in a "S pattern" as it is released. The conductor wire proceeds about frame guide wheel 707 through exit guide 708. As shown in FIG. 7, subassembly 700 includes a plurality of components mounted to frame 703. By mounting the other components in this manner, frame 703 may be rotated thereby controlling the twist applied to the conductor wire as it is released from subassembly 700. The twist applied by rotation of subassemblies 700 is controlled to negate the twist imparted on the wires by rotation about the mandrel or tubing so that a minimal amount of net twist is applied to the final wound product.

In the known automated winding system described in U.S. Pat. No. 7,287,366, a plurality of wire release subassemblies 700 are disposed about a turntable and a plurality of gears underneath the turntables engage the respective subassemblies to rotate the subassemblies 700 relative to the turntable. In operation, a mandrel, insulative tubing, or other work material is drawn through a center of the system and wound onto a final spool structure. Wire release subassemblies 700 are operated to release wire as the mandrel, tubing, or the like is drawn through the center. Concurrently, the turntable is rotated. Further, a number of gears are disposed below the turn table and engage each subassembly 700 to controllably rotate the frames 703 of the subassemblies 700 relative to the turntable thereby controlling the twist on the wires released by the subassemblies.

Figure 8:
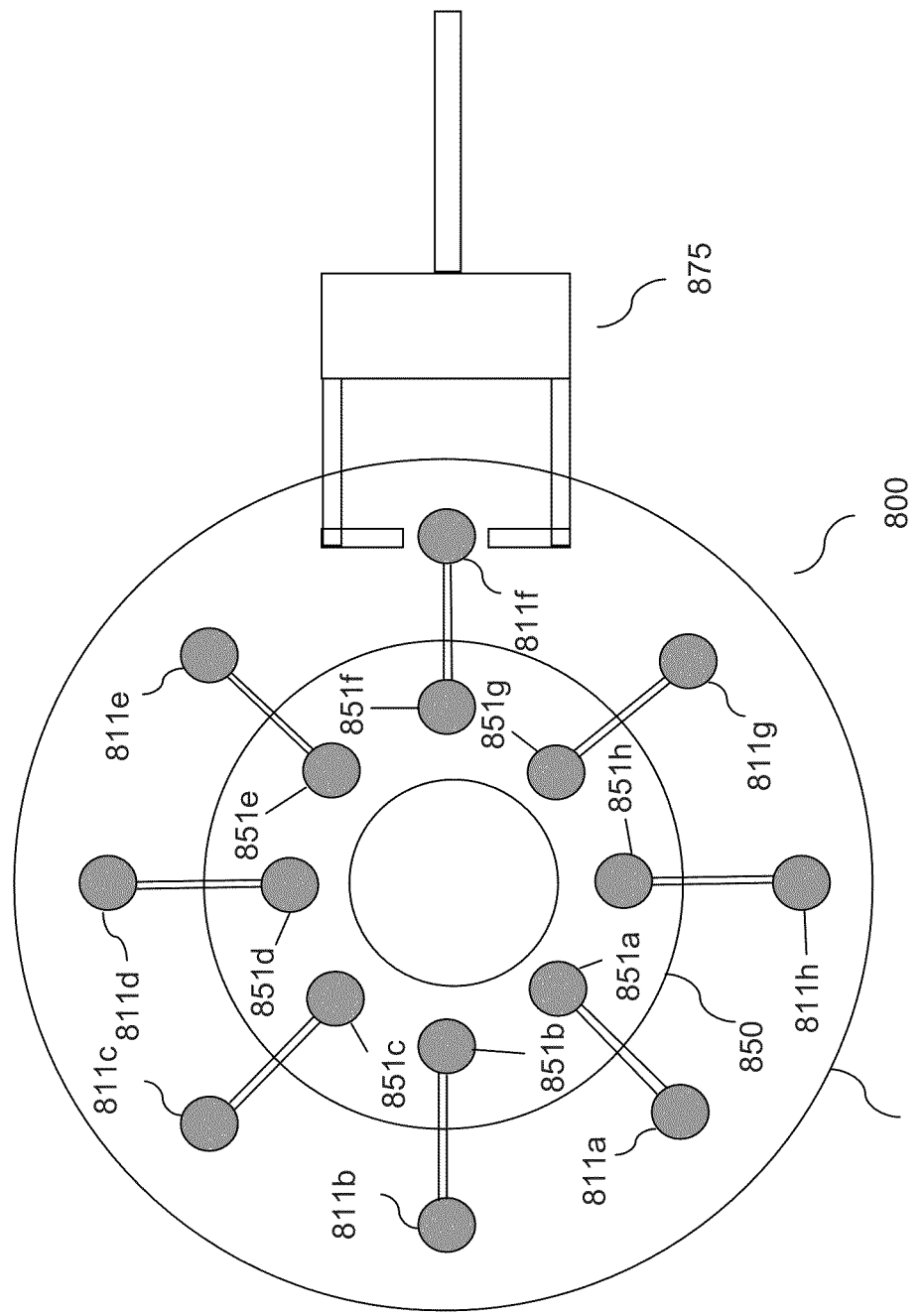
FIG. 8 depicts a subassembly that permits rotation of wire release subassemblies at different rates according to one representative embodiment.

FIG. 8 depicts dual turntable assembly 800 for winding wire conductors according to one representative embodiment. In lieu of a design shown in U.S. Pat. No. 7,287,366 where all of the wire release subassemblies 700 are rotated at the same rate, turntable assembly 800 permits subassemblies 700 to be rotated about the mandrel or tubing at different rates. Turntable assembly 800 comprises outer ring section 810 about inner ring section 850. Outer ring section 810 and inner ring section 850 are independently rotatable.

Outer ring section 810 comprises a plurality of apertures (shown as 811a-811h) through which a drive shaft portion of a respective subassembly 700 may be inserted. Inner ring section 850 likewise comprises a plurality of apertures (shown as 851a-851h) through which a drive shaft portion of a respective subassembly 700 may be inserted. When placed through one of the apertures, a respective subassembly 700 couples with a controllable drive assembly (not shown) which rotates the subassembly 700 to control the twist imparted to the released wire conductor. The controllable drive assemblies are, in turn, mounted on the underside of the respective ring sections 810 and 850.

In operation, the rotation of outer ring section 810 and inner ring section 850 may be halted and outer ring section 810 and inner ring section 850 may be brought into mutual alignment, i.e., corresponding apertures of each section 810 and 850 are aligned. When outer and inner ring sections 810 and 850 are so aligned, placer arm 875 preferably engages a respective subassembly 700, lifts the drive shaft portion from the respective aperture, moves the drive shaft portion radially (inwardly or outwardly), and then places the drive shaft portion into an aperture of the other ring section.

Figure 9:
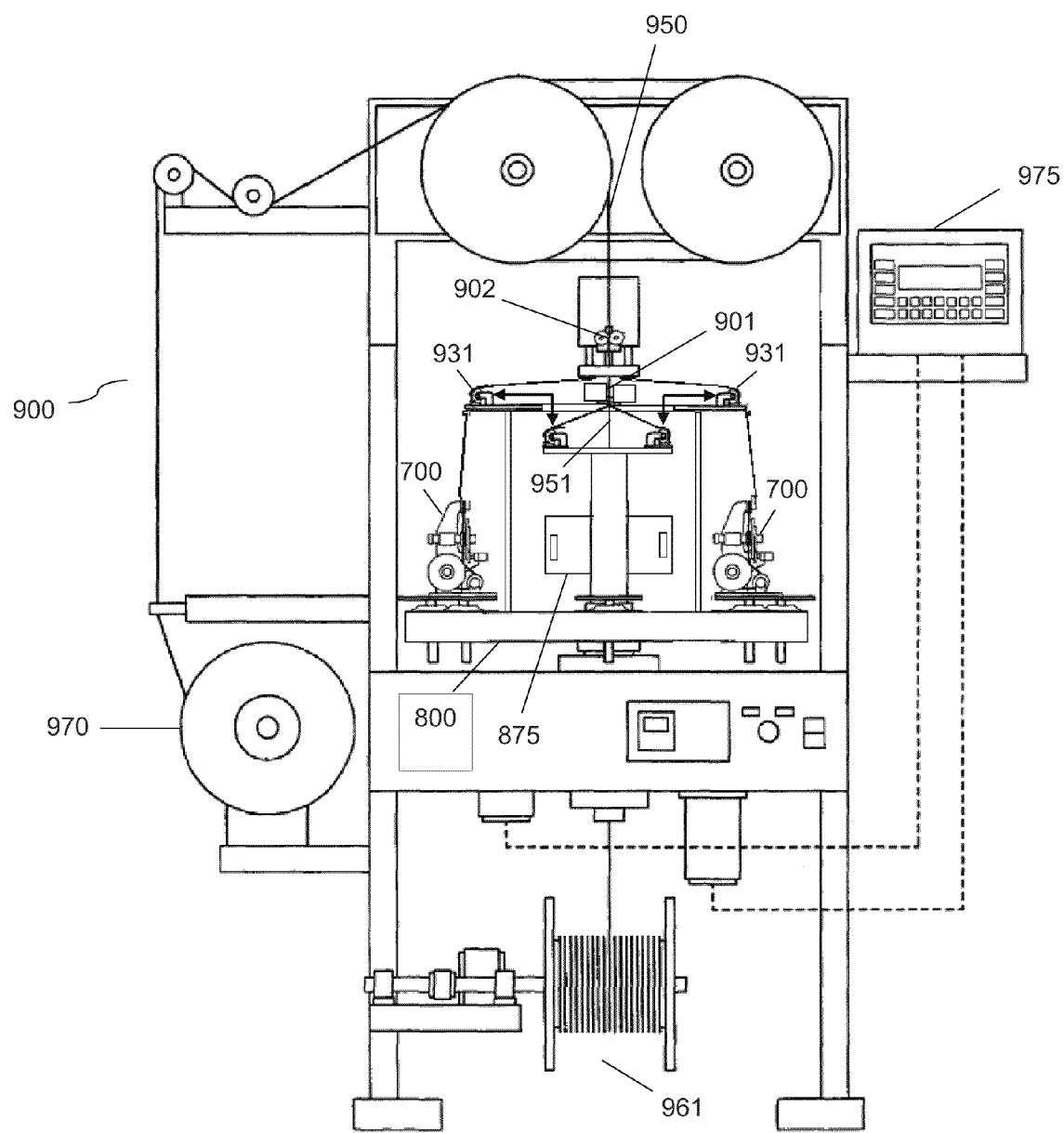
FIG. 9 depicts an automated wire winding system according to one representative embodiment.

FIG. 9 depicts automated winding system 900 according to one representative embodiment. System 900 comprises controller 975. Controller 975 is preferably implemented using a suitable processor, memory, user interface controls, and software. Controller 975 provides control signals to the respective components of system 900 to control their various operations in a coordinated manner.

System 900 comprises payout assembly 961. Payout assembly 961 comprises a substantial length of mandrel or small diameter medical tubing 951 about a spool. System 900 controllably releases the mandrel or tubing 951 about which the wire conductors are wound during operation of system 900.

System 900 comprises dual turntable assembly 800 for rotating wire release subassemblies 700. For the sake of clarity, only two subassemblies 700 are shown about the outer rotatable portion of assembly 800. As previously discussed, subassemblies 700 are moveable between the outer portion and inner portion of subassembly 800. During winding operations, the inner portion of assembly 800 is rotated at a greater angular rate so that a greater number of turns per unit of length of the mandrel or tubing for the inner winding portions are obtained.

System 900 preferably comprises two wire winding zones 901 and 902. In the first wire winding zone 901, the wire conductor(s) released by wire release subassemblies 700 in the inner portion of assembly 800 are wound about mandrel or tubing 951. Thereafter, in wire winding zone 902, the wire conductors released by wire release subassemblies 700 in the outer portion of assembly 800 are wound over the wire(s) wound in zone 901 (if any). To facilitate the dual wire wrapping zones on respective rotatable rings, wire guide wheels 931 are moveable (as shown by arrows) between two positions. Placer arm 875 is employed to automatically move wire guide wheels 931 and wire release subassemblies 700 between the respective positions to transition between different wire wrapping patterns. Before or during such transitions, a small amount of wire conductor may be released by a respective wire release subassembly 700 to permit such movement. Also, during or after movement between positions, any slack in the wire may be taken up by a respective wire release assembly.

Wire wrapped product 952 emerges past wire winding zones 901 and 902 and traverses through a multi-stage path through several wheels and guides. Wire wrapped product is taken up by spool 970.

Further processing may be applied to wire wrapped product to form stimulation leads for use in patients. For example, wire wrapped product 950 may be unspooled from spool 970 at a later time through an extruder for extrusion of an outer coating of material. Segments of wire wrapped product 950 may be cut into respective segments. Electrodes and terminals may then be fabricated on each such segment using any known or later developed fabrication process.

Although certain representative embodiments and advantages have been described in detail, it should be understood that various changes, substitutions and alterations can be made herein without departing from the spirit and scope of the appended claims. Moreover, the scope of the present application is not intended to be limited to the particular embodiments of the process, machine, manufacture, composition of matter, means, methods and steps described in the specification. As one of ordinary skill in the art will readily appreciate when reading the present application, other processes, machines, manufacture, compositions of matter, means, methods, or steps, presently existing or later to be developed that perform substantially the same function or achieve substantially the same result as the described embodiments may be utilized. Accordingly, the appended claims are intended to include within their scope such processes, machines, manufacture, compositions of matter, means, methods, or steps.

The invention claimed is:

1. A method of fabricating a stimulation lead for stimulation of tissue of a patient, wherein the stimulation lead is adapted to reduce tissue heating when present in an MRI system, the method comprising:
   helically wrapping a plurality of conductors about an axis such that each conductor of the plurality of conductors comprises an inner segment of multiple windings and an outer segment of multiple windings relative to the axis, wherein the outer segment comprises a first winding pitch and the inner segment comprises a second winding pitch, the second winding pitch is less than the first winding pitch, the inner segment of each respective conductor being disposed interior to the outer segments of other conductors of the plurality of conductors, an impedance of each conductor at a MRI pulsed RF frequency of the plurality of conductors substantially reduces MRI-induced current when the stimulation lead is present in the MRI system;
   forming a lead body with the helically wrapped plurality of conductors;
   providing a plurality of electrodes that are electrically coupled to the plurality of conductors; and
   providing a plurality of terminals that are electrically coupled to the plurality of conductors.

2. The method of claim 1 wherein the helically wrapping comprising:
   operating a plurality of wire release assemblies to release respective ones of the plurality of conductors from two independently rotating rings.

3. The method of claim 2 further comprising:
   moving respective ones of the plurality of wire release assemblies between the two independently rotating rings.

4. The method of claim 2 further comprising:
   letting out a limited amount of length of a conductor of a respective wire release assembly when moving the respective conductor wire release assembly.

5. The method of claim 2 further comprising:
   taking up an amount of slack of a conductor of respective wire release assembly when moving the respective conductor wire release assembly.

6. The method of claim 1 wherein the helically winding is performed by an automated wire winding system and wherein the helically winding comprises:
   winding the inner segments of the plurality of conductors at a first winding location of the automated wire winding system; and
   winding the outer segments of the plurality of conductors at a second winding location of the automated wire winding system.

7. The method of claim 1 wherein each conductor of the plurality of conductors exhibits an impedance of greater than 2500 Ohms to current flow at 64 MHz.

8. The method of claim 1 wherein the electrodes are ring electrodes.

9. The method of claim 1 wherein the electrodes are segmented electrodes.

10. The method of claim 1 further comprising:
    providing a paddle structure wherein the plurality of electrodes are disposed on the paddle structure.

11. The method of claim 1 wherein each conductor of the plurality of conductors is helically wound to include a plurality of inner segments.

12. The method of claim 11 wherein at least two of the plurality of inner segments are spaced at a distance of ¼ of an MRI frequency.

* * * * *